United States Patent
Oshima et al.

(10) Patent No.: US 9,062,218 B2
(45) Date of Patent: Jun. 23, 2015

(54) DNA-CONTAINING INK COMPOSITION

(75) Inventors: Atsushi Oshima, Otsu (JP); Fumie Yusa, Nagahama (JP)

(73) Assignees: NAGAHAMA BIO-LABORATORY INCORPORATED, Nagahama-Shi (JP); EDUCATION CORPORATION KANSAI BUNRI SOUGOUGAKUEN, Nagahama-Shi (JP)

( * ) Notice: Subject to any disclaimer, the term of this patent is extended or adjusted under 35 U.S.C. 154(b) by 271 days.

(21) Appl. No.: 13/063,732

(22) PCT Filed: Sep. 11, 2008

(86) PCT No.: PCT/JP2008/066450
§ 371 (c)(1),
(2), (4) Date: Jun. 6, 2011

(87) PCT Pub. No.: WO2010/029629
PCT Pub. Date: Mar. 18, 2010

(65) Prior Publication Data
US 2011/0229881 A1    Sep. 22, 2011

(51) Int. Cl.
| | |
|---|---|
| C12Q 1/68 | (2006.01) |
| C09D 7/12 | (2006.01) |
| B41M 3/14 | (2006.01) |
| C09D 11/00 | (2014.01) |
| C09D 11/32 | (2014.01) |
| C12N 15/10 | (2006.01) |
| G07D 7/14 | (2006.01) |
| C08L 89/00 | (2006.01) |

(52) U.S. Cl.
CPC ............. C09D 7/125 (2013.01); B41M 3/14 (2013.01); B42D 2033/20 (2013.01); C08L 89/00 (2013.01); C09D 11/00 (2013.01); C09D 11/32 (2013.01); C12N 15/10 (2013.01); C12Q 1/68 (2013.01); C12Q 1/6806 (2013.01); C12Q 1/6876 (2013.01); C12Q 2563/185 (2013.01); G07D 7/14 (2013.01)

(58) Field of Classification Search
None
See application file for complete search history.

(56) References Cited

U.S. PATENT DOCUMENTS

| | | | | |
|---|---|---|---|---|
| 5,139,812 A | * | 8/1992 | Lebacq | 427/7 |
| 2004/0058374 A1 | | 3/2004 | Sheu et al. | |
| 2005/0226675 A1 | * | 10/2005 | Kwan et al. | 401/35 |
| 2005/0272833 A1 | * | 12/2005 | Doshi | 523/160 |
| 2006/0028521 A1 | * | 2/2006 | Frenkel | 347/100 |
| 2008/0229975 A1 | * | 9/2008 | Auslander et al. | 106/31.86 |

FOREIGN PATENT DOCUMENTS

| | | | | |
|---|---|---|---|---|
| CA | 2175012 | | 10/1996 | |
| JP | 56131680 | * | 10/1981 | ............... C12Q 1/68 |
| JP | 8-302264 A | | 11/1996 | |
| JP | 2002-167530 A | | 6/2002 | |
| JP | 2004-159502 A | | 6/2004 | |
| JP | 2004-175922 A | | 6/2004 | |
| JP | 2004-175923 A | | 6/2004 | |
| JP | 2004-331832 | * | 11/2004 | ............... C12Q 1/68 |
| JP | 2005-247900 A | | 9/2005 | |
| JP | 2006-022300 A | | 1/2006 | |
| JP | 2006-169341 A | | 6/2006 | |
| JP | 2008-187992 A | | 8/2008 | |
| JP | 2008-222966 A | | 9/2008 | |
| WO | WO00/444891 | * | 8/2000 | ............... C12Q 1/68 |

OTHER PUBLICATIONS

English Machine Translation of JP 2006-169341A, Jun. 26, 2006.*
Office Action issued in Japanese Patent Application No. 2007-066961 on Jun. 22, 2012.
International Search Report; Application No. PCT/JP2008/066450; Filed Sep. 11, 2008.
Office Action dated Mar. 1, 2013 in corresponding Japan Application No. 2010-528566.
Office Action issued Jun. 25, 2014 in corresponding Japanese Patent Application No. 2007-066961.

* cited by examiner

*Primary Examiner* — Jeanine A Goldberg
(74) *Attorney, Agent, or Firm* — Knobbe Martens Olson & Bear LLP (57) ABSTRACT

An ink, which contains DNA and is hardly decomposed by an external stimulus such as ultraviolet light, heat, an acid or an alkali, is provided. A method of easily analyzing a DNA in an ink composition is also provided. An ink composition containing a DNA and having a water-tolerance at a certain level or higher is prepared. The DNA in a print that is produced by using the above ink composition is quickly extracted with water or an aqueous solution and analyzed. Furthermore, a DNA in a print that is produced by using an oil- and water-based ink composition containing the DNA is quickly extracted with water or an aqueous solution and analyzed.

6 Claims, 2 Drawing Sheets

Fig. 1

| Lane | Sample | Volume applied (6 × dye 1 μl + sample 5 μl) |
|---|---|---|
| 1 | 100bp DNA ladder | 6 |
| 2 | negative control | 6 |
| 3 | positive control | 6 |
| 4, 5, 6 | ncDNA1, 2, 3 | 6 |
| 7, 8, 9 | Yellow containing DNA, 3 Samples from page 8 | 6 |
| 10, 11, 12 | Yellow containing DNA, 3 Samples from page 9 | 6 |
| 13, 14, 15 | Yellow containing DNA, 3 Samples from page 10 | 6 |

Fig. 2

| Lane | Sample | Volume applied (6 × dye 1 μl + sample 5 μl) |
| --- | --- | --- |
| 1 | 100bp DNA ladder | 6 |
| 2 | negative control | 6 |
| 3 | positive control | 6 |
| 4, 5, 6 | ncDNA1, 2, 3 | 6 |
| 7~11 | Black containing DNA | 6 |
| 12~16 | Black containing DNA, Sample I | 6 |
| 17~21 | Black containing DNA, Sample II | 6 |

DNA-CONTAINING INK COMPOSITION

CROSS-REFERNCE TO RELATED APPLICATIONS

This application is the U.S. National Phase under 35 U.S.C. 0371 of International Application PCT/JP2008/066450, filed Sep. 11, 2008. The International Application was published under PCT Article 21(2) in a language other than English.

TECHNICAL FIELD

The present invention relates to a DNA-containing ink composition which can be used in writing or printing of letters, images, and various codes. More specifically, it relates to a DNA-containing ink composition which is used for printing securities, cards, foods, coating areas of cars, and the like and is suitable for personal authentication or judging the authenticity by vermilion ink-pads or various coloring tools, as well as to a simple method for DNA extraction using the composition.

A Sequence Listing, submitted as an ASCII text file via EFS-Web, is hereby incorporated by reference in accordance with 35 U.S.C. §1.52(e). The name of the ASCII text file for the Sequence Listing is 20279757_1.TXT, the date of creation of the ASCII text file is Mar. 26, 2015, and the size of the ASCII text file is 556 bytes.

BACKGROUND ART

Currently, DNAs are used for personal authentication, for example, in criminal investigation or determination of parentage, utilizing characteristic portions of the DNAs having a high discrimination capacity. Recently, in addition to such applications, a method of judging the authenticity has been considered in which checks, bank bills, various certificates, cards, and the like are, for example, printed with an ink containing a DNA to address the forgery. For example, it is disclosed that a thin-film pattern is formed using a DNA ink for personal identification obtained by mixing a DNA molecule with a cationic surfactant, and the pattern formed is utilized as information for personal identification (see Patent Document 1). In this method, a complicated thin-film pattern formed by thin-filmy spread of the DNA molecule is optically detected as identification information, but characteristic biological information possessed by the DNA molecule is not utilized.

A method of judging the authenticity of a seal or handwriting is also disclosed in which a base sequence of a particular DNA fragment having a predetermined base sequence is used as an indicator (e.g., Patent Document 2). On the other hand, there exists a material which is obtained by incorporating a DNA into a gel substance or a microcapsule made of a plastic resin, for example, by interfacial polymerization, or a material which is obtained by previously binding a DNA onto a surface of an ultrafine particle made of a plastic resin and then mixing the resulting particle with an ink (Patent Documents 3 and 4).

All the above techniques using a DNA-containing ink differ from conventional authentication systems in respect of the use of a DNA, and are noteworthy. However, the DNA contained in the printed ink is often decomposed by an external stimulus such as light, an ultraviolet ray, heat, an acid, and an alkali. Accordingly, when a DNA is directly contained in an ink, the amount of DNA decreases immediately after printing and the detection becomes difficult. On the other hand, when a method of introducing a DNA into a microcapsule and the like or a method of retaining a DNA on a carrier such as a particle is used, the resistance to the external stimulus is improved. However, it takes a long time of one day or more to detect, for example, a DNA in an ink after printing as it is now.

Patent Document 1: JP-A-2002-167530
Patent Document 2: JP-A-2005-247900
Patent Document 3: JP-A-2004-175922
Patent Document 4: JP-A-2004-331832

DISCLOSURE OF THE INVENTION

Problems to be Solved by the Invention

As described above, DNAs have a problem that they easily decompose by action of an ultraviolet ray, heat, an acid, an alkali, and the like, and have a possibility that, when they are mixed into an ink and used for the preparation of a printed matter, they can no longer be discriminated at the time of analysis. In addition, the recovery of a DNA after printing needs multiple steps and is attended with difficulty. In spite of the need to establish a DNA ink composition, which retains a good discrimination capacity of a DNA after printing and allows for application of a rapid and simple method at the time of analysis, as well as a method for analyzing the DNA, such an ink composition and a method for reliably detecting a DNA have not been found. Accordingly, means for solving the above problems have been required.

Means for Solving the Problems

The present inventors have intensively studied so as to provide a DNA-containing ink composition, which can tolerate an external stimulus such as an ultraviolet ray, heat, an acid, and an alkali, as well as a simple method for detecting a DNA. As a result, they have found an ink composition which is resistant to an external stimulus and allows for simple extraction of a DNA after printing, have established a detection method and the like using the ink composition, and thus have completed the present invention.

That is, the present invention provides a waterproof ink composition including a DNA.

The waterproof ink composition may be a mixture of a waterproof ink and a DNA.

The waterproof ink composition may be a composition including water, a colorant, a resin, and a DNA.

The resin may be at least one selected from the group consisting of a urethane resin, an acrylic resin, and an epoxy resin.

The content of the DNA may be $3 \times 10^{-10}$ μg or more and 20 μg or less per 1 μl of the ink composition.

The present invention also provides a method of extracting a DNA from a print on a medium, which includes the step of bringing a print, which is prepared using any one of the ink compositions, into contact with water or an aqueous solution.

The medium may be one selected from the group consisting of paper, a plastic resin, a fabric, a metal, and a food.

The present invention further provides a method of judging the authenticity of a print on a medium, which includes the steps of:

bringing a print, which is prepared using any one of the ink compositions, into contact with water or an aqueous solution;

preparing an aqueous DNA-containing solution obtained by bringing the print into contact with water or an aqueous solution; and analyzing the DNA in the aqueous DNA-containing solution prepared.

The medium may be one selected from the group consisting of paper, a plastic resin, a fabric, a metal, and a food.

The present invention also provides a method of extracting a DNA from a print on a medium, which includes the step of bringing a print, which is prepared using an oil-based ink or a water-based ink composition containing the DNA, into contact with water or an aqueous solution.

The medium may be one selected from the group consisting of paper, a plastic resin, a fabric, a metal, and a food.

The present invention further provides a method of judging the authenticity of a print on a medium, which includes the steps of:

(1) bringing a print, which is prepared using an oil-based ink or a water-based ink composition containing a DNA, into contact with water or an aqueous solution;

(2) preparing an aqueous DNA-containing solution obtained by bringing the print into contact with water or an aqueous solution; and (3) analyzing the DNA in the aqueous DNA-containing solution prepared.

The medium may be one selected from the group consisting of paper, a plastic resin, a fabric, a metal, and a food.

Effects of the Invention

The waterproof ink composition according to the present invention is resistant to an external stimulus such as an ultraviolet ray, heat, an acid, and an alkali, and can suppress the proportion of decomposed DNAs to a low extent even after a printed matter is allowed to stand for a long time. Also, DNAs in the ink composition can be extracted with water or an aqueous solution in a short time and in a simple manner. Furthermore, if the waterproof ink composition according to the present invention is used, DNAs can be recovered over several times from the same printed matter. Accordingly, the waterproof ink composition according to the present invention can be used to establish a very excellent system for judging whether a printed matter is real or fake, for example.

It has also been found in the present invention that DNAs in an ink composition can be extracted with water or an aqueous solution even in an oil-based ink or a water-based ink composition containing the DNAs. Thus, by applying the present method, it becomes possible to carry out extraction and analysis of DNAs in a simpler manner than before.

BEST MODE FOR CARRYING OUT THE INVENTION

The present invention will be described in detail below.

The term "waterproof ink composition" used in the present invention refers to an ink composition which does not fall into categories of the conventional water-based ink and oil-based ink, and can be expressed as "waterproof". When the term "waterproof ink composition" is used in the present specification, it refers to a composition which contains a DNA, a colorant such as a dye or a pigment, a resin as a fixing material for a dye or a pigment, and water, and appropriately other additives such as an antiseptic agent, a water-soluble organic solvent, a surfactant and a pH buffer, and the composition satisfies the following conditions.

That is, it refers to an ink composition which can contain, or is miscible with, water at a normal temperature (25° C.) in an amount of 5% by weight or more per ink composition, and which shows no penetration of the ink into a polyester cloth and no observation of blur in a printed matter when the printed matter is immersed in water, tap water, distilled water, deionized water, etc., at a normal temperature (25° C.) for 48 hours, and then removed and rubbed with a 100% polyester cloth, and exfoliation of the ink is examined. When the ink easily penetrates into the polyester cloth, or blur is observed in the printed matter, the composition falls into "water-based ink composition".

DNAs contained in the present ink composition are not limited to particular ones. For example, it is possible to use both natural DNAs derived from genes of human, animals or microorganisms and synthetic DNAs. Also, it is possible to use both single-stranded and double-stranded DNAs. Molecular weights of the DNAs are not limited as well, and it is possible to use short-chain DNA fragments having about 10 bases to medium- and long-chain DNA fragments having 200 or more bases. Usually, it is easy to use DNA fragments having about 20 to about 100 bases. The DNAs may be selected from these fragments suitably depending on the intended use. When natural DNAs are used, it is possible to use gene regions or intergenic regions such as microsatellite regions among base sequences of whole DNAs in cells. When synthetic DNAs are used, it is possible to obtain desired DNAs, for example, by synthesizing them using a commercially available DNA synthesizer, and then purifying them. The desired DNAs may have the same, analogous or quite different sequences as compared with natural DNAs, and all the sequences can be used in the present invention suitably. In the above description, the ink composition refers to any of a waterproof ink composition, an oil-based ink composition and a water-based ink composition.

The content of DNA fragments in the present invention is $3 \times 10^{-10}$ µg or more and 20 µg or less, preferably from 1 ng to 1 µg, and more preferably from 10 ng to 5,000 ng, per 1 µl of the ink composition. Herein, the ink composition refers to any of a waterproof ink composition, an oil-based ink composition and a water-based ink composition.

The waterproof ink composition according to the present invention is not limited to particular one, and can be prepared by mixing a DNA with a commercially available waterproof ink. Alternatively, the waterproof ink composition may be prepared by mixing a DNA, a colorant such as a dye or a pigment, a resin as a fixing material for a dye or a pigment and water, and appropriately other additives such as an antiseptic agent, a water-soluble organic solvent, a surfactant, and a pH buffer.

In this connection, the term "waterproof ink" used in the present invention refers to a waterproof ink which does not fall into categories of a conventional water-based ink and oil-based ink and can be expressed as "waterproof". When the term "waterproof ink" is used in the present specification, preferably, it refers to an ink which contains a colorant, a resin as a fixing material for a dye or a pigment and water, and appropriately other additives such as an antiseptic agent, a water-soluble organic solvent, a surfactant, and a pH buffer. The "waterproof ink" in the present invention satisfies the following parameters.

That is, it refers to an ink which can contain, or is miscible with, water at a normal temperature (25° C.) in an amount of 5% by weight or more per ink, and which shows no penetration of the ink into a polyester cloth and no observation of blur in a printed matter when the printed matter is immersed in water (tap water, distilled water, deionized water, etc.) at a normal temperature (25° C.) for 48 hours, and then removed and rubbed with a 100% polyester cloth, and exfoliation of the ink is examined. When the ink easily penetrates into the polyester cloth, or blur is observed in the printed matter, the ink falls into "water-based ink".

Also, the "waterproof ink" may contain 44.0 to 46.0% by weight of a nonvolatile component, and have a viscosity of 75 to 700 (CP/25° C.) and a pH of 7.5 to 9.0 (25° C.), for example, without being limited thereto. In this case, the viscosity is determined by measuring a viscosity of a composition temperature-adjusted at 25° C. using a BH type rotatory viscometer (TOKIMEC Inc.) and a rotor at a rotation number of 20 rpm.

The term "oil-based ink" used in the present specification refers to a conventional oil-based ink which contains an oil-soluble resin, an organic solvent such as alcohol, a pigment or a dye, has a quick-drying property and does not dissolve in water. It refers to an ink which can not contain (is not miscible with) water at a normal temperature (25° C.) in an amount of 5% by weight or more per ink, and which shows no penetration of the ink into a polyester cloth and no observation of blur in a printed matter when the printed matter is immersed in water (tap water, distilled water, deionized water, etc.) at a normal temperature (25° C.) for 48 hours, and then removed and rubbed with a 100% polyester cloth, and exfoliation of the ink is examined.

The colorant contained in the waterproof ink composition according to the present invention may be a dye or a pigment. Also, a transparent ink may be used by selecting the type of the pigment.

The dye may be used by directly dissolving in an ink as a constituent, or after allowing it to be carried on or contained in an inorganic or organic microparticle.

The dye contained in the waterproof ink composition according to the present invention may be used after being mixed with other coloring materials, if necessary. It is possible to use, as a water-soluble dye, a dye which is classified into an acidic dye, a direct dye, a basic dye, a reactive dye, and a food dye in color index and which is superior in water resistance and light resistance.

The colorant contained in the waterproof ink composition according to the present invention may be an organic pigment or an inorganic pigment. The organic pigment includes azo, phthalocyanine, anthraquinone, dioxazine, indigo, thioindigo, perylene, isoindolenone, aniline black and azomethine, a rhodamine B lake pigment, and carbon black. The inorganic pigment includes iron oxide, titanium oxide, calcium carbonate, barium sulfate, aluminum hydroxide, barium yellow, iron blue, cadmium red, chrome yellow, and a metal powder.

The resin as a fixing material for a dye or a pigment used for the preparation of the waterproof ink according to the present invention is not limited to particular one as long as the resin is one usually used for the preparation of a waterproof ink, and preferably includes a urethane resin, an acrylic resin and an epoxy resin. The content of the resin is preferably from 3% by weight to 70% by weight, and more preferably from 5% by weight to 50% by weight, relative to the ink composition as a whole.

The waterproof ink composition according to the present invention may contain a surfactant as its constituent. The surfactant can improve wettability in recording paper. Preferable surfactants include, for example, polyoxyethylene alkyl ether acetate, dialkyl sulfosuccinate, polyoxyethylene alkyl ether, polyoxyethylene alkylphenyl ether, a polyoxyethylene-polyoxypropylene block copolymer, and an acetylene glycol surfactant.

In addition, the surfactant exhibits an excellent stability of soluble state by using a lithium ion, or a quaternary ammonium or a quaternary phosphonium as a counter ion of the surfactant used in the present invention.

Moreover, the waterproof ink composition according to the present invention may contain a penetrating agent as its constituent for the purpose of adjusting the surface tension.

Furthermore, any substance may be used as a pH-adjusting agent, providing that the substance can suitably adjust the pH without adversely affecting a prepared ink. Examples thereof include amines such as diethanolamine, and triethanolamine, hydroxides of alkali metal elements, such as lithium hydroxide and sodium hydroxide, ammonium hydroxide, quaternary ammonium hydroxides, quaternary phosphonium hydroxides, and carbonates of alkali metals, such as lithium carbonate, sodium carbonate, and potassium carbonate.

Also, the DNA ink composition according to the present invention may contain a conventionally known antiseptic-antimold agent, an antirust agent and other additives. For example, the antiseptic-antimold agent such as sodium dehydroacetate, sodium sorbate, sodium 2-pyridinethiol-1-oxide, sodium benzoate, sodium pentachlorophenolate, and isothiazoline may be used in the present invention.

The antirust agent includes, for example, acidic sulfite, sodium thiosulfate, ammonium thiodiglycolate, diisopropyl ammonium nitrite, pentaerythritol tetranitrate, and dicyclohexyl ammonium nitrite.

Furthermore, it is possible to add to the ink composition a water-soluble ultraviolet absorber, a water-soluble infrared absorber, and a defoamer depending on the intended use.

The defoamer includes, for example, those based on fats, fatty acids, fatty acid esters, alcohols, phosphate esters, amines, amides, metal soaps, sulfate esters, and silicones. They can be used alone or in combination of two or more substances. Among them, a silicone defoamer having a siloxane bond is preferred from the viewpoint of easy control of negative pressure of a sponge absorber in an ink tank. In particular, a polysiloxane defoamer having polyethylene oxide and/or polypropylene oxide added is effective.

Moreover, the waterproof ink composition according to the present invention may contain alcohols. The alcohols include methanol, ethanol, and isopropanol, and the content of alcohols may be in a range of 0% by weight to 70% by weight relative to the ink composition as a whole.

It is possible to prepare a discriminable document, a printed matter and the like by suitably printing the present DNA-containing ink composition prepared as described above on a medium. In this connection, the term "printing" includes not only an aspect in which an ink is used for printing but also an aspect in which an ink is coated on a medium or used for hand writing of letters and the like on a medium. The medium used in this case may be one selected from the group consisting of paper, a plastic resin, a fabric, a metal, and a food, but is not limited thereto. Thus, it is possible to use all media which can be used for a usual printed matter. The printed matter and the like thus prepared can stably retain DNAs for a long time even when it is handled in the same way as previously. Also, the recovery is easy and rapid detection is possible.

That is, it is possible, for example, in the present invention, to extract or analyze DNAs easily by bringing the print thus obtained on a medium into contact with water or an aqueous solution. In this connection, the aqueous solution refers to various buffered solutions prepared by adding to water a component which does not influence a resin component contained in an ink, a solution for PCR, a solution for DNA hybridization or their equivalents. The procedure can be applied most conveniently to the print prepared using the waterproof ink composition, but also applied to a DNA-containing oil-based ink composition or water-based ink composition by setting conditions.

The contact with water or an aqueous solution can be carried out by dropping a droplet directly on the print and allowing to stand for a short time, for example, for about 1 second to 1 hour, in a simple case for about 10 seconds to 1 minute. The contact with water or an aqueous solution may be carried out for an even longer time not exceeding 48 hours, if necessary.

After allowing to stand, it is possible to recover the water or the aqueous solution, to amplify DNAs contained therein by a PCR method or the like, and to analyze the DNAs in a short time. It is also possible to carry out hybridization directly between the recovered solution and a probe.

Alternatively, it is possible to cut off a printed portion together with a medium such as paper, to add them directly to a solution for PCR or the like, and to carry out the PCR.

In the print prepared using the present DNA-containing ink composition, it is possible to judge whether the print is real or fake, by utilizing the discrimination capacity of the DNA. The method includes bringing the print, prepared using the present ink composition, into contact with water or an aqueous solution such as a buffered solution, recovering the resulting aqueous DNA-containing solution, and analyzing the DNA in the aqueous solution. The method can be applied most conveniently to the print prepared using the waterproof ink composition, but also applied to a DNA-containing oil-based ink composition or water-based ink composition by setting conditions.

After amplifying the DNA by a PCR method, the analysis can be carried out by a method of confirming the size of a DNA fragment using agarose gel electrophoresis, or by a method of determining a base sequence to confirm a predefined DNA, although the analysis is not limited to such a method. Alternatively, it is also preferable to simply detect the DNA by a hybridization method using a labeled probe or the like. Specifically, a synthetic DNA having a sequence complementary to a portion of a target DNA is previously prepared, hybridization is carried out under a certain condition, and the presence or absence of the formation of a double-stranded DNA can be discriminated, for example, by the presence or absence of discoloration by a colloidal gold solution, or by a fluorescent reagent such as SYBR Green or SYBR Safe.

The PCR method per se is well known, and a kit and an apparatus for the method are commercially available. Accordingly, the method can be carried out easily after synthesizing a forward primer and a reverse primer used. Also, the discriminating probe is well known, and therefore, the above method can be carried out easily after synthesizing the probe suitably depending on the sequence of a target DNA. A specific method is specifically described in the following Examples.

The present invention will be specifically described by way of the following Examples, but these Examples do not intend to limit the technical scope of the present invention. Those skilled in the art can easily make modifications and variations to the present invention on the basis of the description in the specification, and such modifications and variations are included in the technical scope of the present invention.

EXAMPLES

The DNA used in the following Examples and Comparative Examples was prepared by purifying and desalting 85-mer:

(ATTAACCCTCACTAAAGGGATCAATAAAACAAAACAAAACGCGCGG

CTCACGGGCGCCTAGGAGTGCCCTATAGTGAGTCGTATT)

as shown in SEQ ID NO:1 of the Sequence Listing using a reverse-phase cartridge column. In all cases, the PCR was carried out using Bio Taq DNA Polymerase obtained from Bioline Co., Ltd. under the condition recommended by Bioline Co., Ltd.

Example 1

Preparation of Waterproof Ink Composition

A waterproof ink (transparent: available from Osaka Sealing Printing Co, Ltd.) was mixed with each of DNA solutions (DNA concentrations: 10 µg/µl, 1 µg/µl, 100 ng/µl, and 10 ng/µl; TE (10 mM Tris-HCl, 1 mM EDTA, pH 8.8)) in the proportion of 1:1 to obtain waterproof ink compositions having a final DNA concentration of 5 µg/µl, 500 ng/µl, 50 ng/µl, and 5 ng/µl, respectively.

Example 2

Preparation of Waterproof Ink Composition

A waterproof ink (transparent: available from Osaka Sealing Printing Co, Ltd.) was mixed with each of DNA solutions (DNA concentrations: 10 µg/µl and 1 µg/µl; TE (10 mM Tris-HCl, 1 mM EDTA, pH 8.8)) in the proportion of 99:1 to obtain waterproof ink compositions having a final DNA concentration of 100 ng/µl, and 10 ng/µl, respectively.

Example 3

Waterproof ink compositions were obtained in the same manner as in Example 1, except for using a black ink (black ink for comics, waterproof BLACK4 obtained from DELETER Inc.) as a waterproof ink.

Example 4

Waterproof ink compositions were obtained in the same manner as in Example 2, except for using a black ink (black ink for comics, waterproof BLACK4 obtained from DELETER Inc.) as a waterproof ink.

Comparative Example 1

Preparation of Ink Composition Containing Oil-Based Ink and DNA

Three g of an oil-based transparent ink (oil-based transparent ink brown, oil-based transparent ink white: Sakata Inx Corp.) was mixed with 10 µl of a DNA solution (10 µg DNA/µl TE (10 mM Tris-HCl, 1 mM EDTA, pH 8.8)) for about 30 seconds to obtain an oil-based ink composition having a final DNA concentration of 33 µg/g.

Comparative Example 2

Preparation of Ink Composition Containing Oil-Based Ink and DNA

Two hundred μl of toluene was added to and simply mixed with 10 mg of the oil-based ink composition of Comparative Example 1 to obtain an oil-based DNA ink composition having a final DNA concentration of 1.15 ng/μl.

Comparative Example 3

Two hundred μl of toluene was added to and well mixed with 10 mg of an oil-based transparent ink (oil-based transparent ink brown, oil-based transparent ink white: Sakata Inx Corp.). The resulting mixture was mixed with 0.33 μl of a DNA solution (1 μg DNA/μl TE (10 mM Tris-HCl, 1 mM EDTA, pH 8.8)) for about 30 seconds to obtain an oil-based ink composition having a final DNA concentration of 1.15 ng/μl.

Comparative Example 4

Preparation of Ink Composition Containing Water-Based Ink and DNA

An undiluted solution of a water-based black ink (black ink for comics, water-based BLACK3 obtained from DELETER Inc.) was mixed with each of DNA solutions (DNA concentrations: 10 μg/μl, 1 μg/μl, 100 ng/μl and 10 ng/μl; TE (10 mM Tris-HCl, 1 mM EDTA, pH 8.8)) in the proportion of 1:1 to obtain water-based ink compositions having a final DNA concentration of 5 μg/μl, 500 ng/μl, 50 ng/μl, and 5 ng/μl, respectively.

Comparative Example 5

A black ink (black ink for comics, water-based BLACK3 obtained from DELETER Inc.) was used as a water-based ink and mixed with a DNA solution (10 μg/μl TE (10 mM Tris-HCl, 1 mM EDTA, pH 8.8)) in the proportion of 99:1 to obtain a waterproof ink composition having a final DNA concentration of 100 ng/μl.

The types of inks and the contents of the DNA in the Examples and Comparative Examples are as shown in Table 1.

Next, an attempt to recover and purify a DNA from the resulting paper printed with the DNA-containing ink was made. First, 1 cm$^2$ pieces were cut off from the applied area using a disposal razor, and they were further cut finely to collect the sections.

To the sections, 500 μl of water was added, and then, 400 μl of toluene and 100 μl of methyl isobutyl ketone were further added to and well mixed with the mixture. After allowing to stand for 30 minutes at room temperature, the mixture was centrifuged for 5 minutes. When the mixture separated into an organic layer and an aqueous layer, the aqueous layer (lower layer) was recovered, and purified by phenol/chloroform extraction and ethanol precipitation. The procedures were carried out at room temperature. In order to confirm whether the recovered material contains a desired DNA, a PCR method was carried out.

As a result, it was found that, in the case of the composition of Example 1 using a waterproof ink composition, about 25% to 30% of the DNA based on the original DNA weight can be recovered in the procedures at room temperature, but in the case of the compositions of Comparative Examples 2 and 3, there exist a case in which the recovery of the DNA is confirmed and a case in which the recovery is not confirmed (Comparative Example 2: one of four runs; Comparative Example 3: one of two runs). Also, for the purpose of improving the recovery method in the compositions of Comparative Examples 2 and 3, the DNA was recovered using a commercially available thinner (Paint Thinner S, Asahipen Corp.). However, substantial changes were not found in the results, and certainty of the recovery per se was poor. It is thought that a DNA can not dissolve evenly in an ink prepared using an oil-based ink and an organic solvent due to a difference in polarity, and unevenness is generated in a DNA concentration in the ink.

Next, the recovered amount was determined by adding 500 μl of water to the sections cut off without using an organic solvent, allowing the mixture to stand for 30 minutes at room temperature, purifying its solution by phenol/chloroform extraction and ethanol precipitation, and measuring an

TABLE 1

| | Example 1 | Example 2 | Example 3 | Example 4 | Comparative Example 1 | Comparative Example 2 | Comparative Example 3 | Comparative Example 4 | Comparative Example 5 |
|---|---|---|---|---|---|---|---|---|---|
| Type of ink | Waterproof, transparent | | Waterproof, Black | | Oil-based (white, brown) | | | Water-based, black | |
| Content of DNA | 5 μg/μl 500 ng/μl 50 ng/μl 5 ng/μl | 100 ng/μl 10 ng/μl | 5 μg/μl 500 ng/μl 50 ng/μl 5 ng/μl | 100 ng/μl 10 ng/μl | 33 μg/g | 1.15 ng/μl | | 5 μg/μl 500 ng/μl 50 ng/μl 5 ng/μl | 100 ng/μl |
| Other components | TE | | TE | | TE | TE, Toluene | | TE | |

Comparison of DNA recovery rate from a printed matter, evaluation of DNA extraction time and recovery rate, analysis of resistance to an ultraviolet ray, and evaluation of multiple DNA recoveries were carried out using the ink compositions obtained in the Examples and Comparative Examples.

(Comparison of DNA Recovery Rate)

At first, each of the ink compositions was applied on paper (copy paper, Just Corp.) using a brush, and the paper was well dried overnight at room temperature in the dark. However, the oil-based ink composition of Comparative Example 1 had a very high viscosity, and therefore, it did not well fit in with the paper after applying. Thus, the application per se of the composition was difficult.

amount of a DNA contained. When a DNA is recovered using water alone, about 35% to 40% of the DNA based on the original DNA weight can be recovered in the procedures at room temperature in the case of the composition of Example 1, but the recovery of the DNA can not be confirmed in the case of the compositions of Comparative Examples 2 and 3.

(Evaluation of DNA Extraction Time and Recovery Rate)

Next, the recovery with water was evaluated by varying the extraction time. As for the ink composition of Example 1, the DNA recovery rate was measured using the extraction times of 2, 5, 10, 20, and 30 minutes (four times for the period "30 minutes", and twice for other periods), and average values were calculated. The results are shown in Table 2.

TABLE 2

| | Extraction time (min.) | | | | |
|---|---|---|---|---|---|
| | 2 | 5 | 10 | 20 | 30 |
| Recovery rate (%) | 36 | 25.5 | 33.5 | 27.5 | 37.5 |

On the other hand, as for the compositions of Examples 2 and 4, 0.2 μl of the composition having a final DNA concentration of 100 ng/μl was spotted on a 4 mm$^2$ area, the spot was dried at 60° C. for 16 hours and then allowed to stand at room temperature for 10 minutes, 10 μl of water was put on the cooled spot and allowed to stand for 10 seconds, pipetting was carried out on the spot, water was recovered once and held for 20 seconds, the same water was again put on the spot, pipetting was carried out, and the amount of the DNA contained in this water was measured. As for the composition of Example 2, the amount was measured five times and the average value was calculated. As a result, it was found that 36.8% of the DNA was recovered. When a PCR was carried out using 1 μl of the recovered solution, amplification was observed in all five PCRs carried out on both the compositions of Examples 2 and 4. When the same experiment was carried out on the composition of Comparative Example 5, amplification by the PCR was not observed.

As is apparent from the above results, even several minutes of the DNA extraction time is sufficient when the waterproof ink composition according to the present invention is used. Thus, it has found that several minutes are sufficient for a necessary extraction time. The results also suggest contrarily that the printed DNA easily leaks out. Accordingly, the following evaluation was carried out.

(Multiple Recoveries of DNA)

Each 0.2 μl of the compositions of Examples 2 and 4 having a final DNA concentration of 100 ng/μl was spotted on a 4 mm$^2$ area, the spot was dried at 150° C. for 10 minutes, the DNA was once recovered from the spot using 1 μl of water, the spot was again dried at 150° C. for 10 minutes, the DNA was recovered using another 1 μl of water, the procedures were repeated five times, and the possibility of amplification by the PCR of the DNA in the recovered solutions was examined. As a result, an amplification amount similar to that observed in the first recovered solution was observed even in the fifth recovered solution, as for the waterproof transparent ink of Example 2. On the other hand, in the case of the waterproof black ink of Example 4, the amplification amount extremely decreased in the PCR using the fourth extract, and no band was sometimes confirmed in the fifth and later extracts. It was found that the amplification was observed even in the sixth extract in the case of the waterproof transparent ink. On the other hand, it was found in the case of the waterproof black ink that the amplification was predominantly observed even in the sixth extract, but the results fell into cases in which the amplification was not observed and cases in which the amplification was observed in a small amount. Consequently, it is thought that the waterproof transparent ink allows analysis on the same printed surface any number of times and the waterproof black ink allows such analysis 3 or 4 times. Also, it is thought that the treatment with a small amount of water, particularly in the case of the waterproof transparent ink, leads to leakage of a small amount of a DNA but the leakage does not occur in an amount which makes the analysis impossible. When waterproof verification is carried out, particularly in the waterproof transparent ink (Example 2), by treating the spot with running water (tap water) for 48 hours, rubbing it with a polyethylene cloth, drying it again, recovering a DNA from the spot using 20 μl of water and confirming the DNA by the PCR, the DNA was observed in all three verifications.

(Practice of Direct PCR Method from Print)

Next, each 2 μl of the compositions of Examples 1 to 4 was applied on a 1 cm$^2$ area using Pipetman as evenly as possible, and the coated paper was dried overnight at room temperature in the dark. Then, a 4 mm$^2$ piece was cut off using a razor, and a PCR was carried out using the paper piece. It was assumed that each PCR tube included, as a template, 0.4 ng, 4 ng, 40 ng or 400 ng of a DNA in Examples 1 and 3, and 0.8 ng or 8 ng of a DNA in Examples 2 and 4. When the PCR products were examined by an agarose electrophoresis, amplification was confirmed in all cases using the compositions of Examples 1, 2, and 3, but not observed in all cases using the compositions of Example 4. As a result, it was found that amplification of a DNA by the PCR can be carried out using a 4 mm$^2$ paper piece per se applied with a waterproof transparent DNA ink as a template, but in the case of a waterproof black DNA ink, the amplification can not be carried out when the DNA concentration is extremely low. Also, the amplification was not observed in all cases using the compositions of Comparative Example 4 under conditions assumed that each PCR tube included, as a template, 0.4 ng, 4 ng, 40 ng or 400 ng of a DNA.

(Evaluation of Resistance to Environment)

Furthermore, in order to evaluate whether improvement of resistance to environment can be expected actually by increasing the content of an ink, resistance to an ultraviolet ray which was considered to have the largest impact on a DNA was examined. To the ink compositions of Examples 1 to 3, or those after drying at 60° C. for 16 hours, ultraviolet irradiation was commenced, a 4 mm$^2$ piece was cut off every few hours using a disposal razor, and the paper piece was put in a PCR tube. Since the PCR in which a paper piece was put in was impossible in the case of the compositions of Example 4, 0.2 μl was spotted on a 4 mm$^2$ area, ultraviolet irradiation was commenced, 1 μl of water was put on the spot every few hours for 10 seconds, pipetting was lightly carried out on the 4 mm$^2$ area, the resulting solution was then recovered and put in a PCR tube, and the PCR was carried out to evaluate whether amplification of the target DNA was possible or not. As a result, it was found that in some cases of Examples 1 and 3, the amplification was not confirmed after 24 hours. On the other hand, in the case of the waterproof transparent inks, even in the amount of 8 ng and also its one-tenth amount of 0.8 ng per 4 mm$^2$ (Example 2), the amplification by the PCR was reliably confirmed after 24 hours of ultraviolet irradiation and sometimes confirmed even after 48 hours irradiation, although a band showing the amplification was not confirmed after 72 hours irradiation. In addition, in the case of the waterproof black DNA inks, in the amount of 20 ng and 2 ng per 4 mm$^2$ (Example 4), the amplification by the PCR was reliably confirmed even after 48 hours of ultraviolet irradiation, and also after 72 hours irradiation.

On the other hand, by way of comparison, a DNA solution per se was diluted with water to final DNA concentrations of 100 ng/μl and 10 ng/μl, each 0.2 μl of the solutions was spotted on a 4 mm$^2$ area, ultraviolet irradiation was commenced, 1 μl of water was put on the spot every few hours for 10 seconds, pipetting was lightly carried out on the 4 mm$^2$ area, the resulting solution was then recovered and put in a PCR tube, and the PCR was carried out to evaluate whether amplification of the target DNA was possible or not. As a result, it was found that a case in which a band showing the amplification was not confirmed after 24 hours of ultraviolet irradiation was produced.

Example 5

Next, ink compositions were prepared using a commercially available oil-based blue ink with the same single-stranded DNA having 85 bases as that used in the above Examples and Comparative Examples in five-level concentrations (300 ng DNA/g ink, 100 ng DNA/g ink, 30 ng DNA/g ink, 10 ng DNA/g ink, and 3 ng DNA/g ink). In preparing the compositions, the DNA and the inks were mixed for 10 minutes under conditions in an ink factory level so that they were mixed well. Then, 64 letters ("K") were printed every 50 sheets of A4 paper using each of the above 5 inks having different DNA concentrations, and the sheets were tested for resistance to environment with ultraviolet irradiation.

UV light used in a conventional germicidal lamp was used to irradiate the printed matters for 0, 6, 18, 35, 45, and 95 hours. In the irradiated samples, the DNA was recovered by direct DNA transfer with water in several tens of seconds without damage of the printed matters. The DNA was amplified by a PCR method and the presence or absence of the DNA was confirmed by agarose gel electrophoresis. As a result, the relationship between the DNA concentration in the ink and the resistance to ultraviolet rays was as follows.

TABLE 3

| DNA concentration | Time of ultraviolet irradiation (hours) | | | | | |
|---|---|---|---|---|---|---|
| | 0 | 6 | 18 | 35 | 45 | 98 |
| 300 ng/g ink | + | + | + | + | + | − |
| 100 ng/g ink | + | + | + | − | − | − |
| 30 ng/g ink | + | + | − | + | − | − |
| 10 ng/g ink | + | + | + | − | − | − |
| 3 ng/g ink | + | + | + | + | +? | +? |

+: Specific amplification was well recognized
−: Specific amplification was not recognized
+: Amplification was recognized but nonspecific amplification was also observed
?: Data were not reliable Although there remains a possibility that the ink does not mix with the DNA completely, it is thought that practically usable printing is possible using a DNA concentration of 100 ng/g ink. Also, there is a possibility that the DNA concentration can be decreased to 30 ng/g ink by completing the mixing of the ink and the DNA.

Example 6

Similar experiments were carried out, except for using a water-based ink for ink-jet (Shachihata Inc.: yellow, black). A DNA was mixed with the water-based ink for ink-jet (yellow or black) to obtain a concentration of 100 ng/μl.

An empty ink-jet cartridge (Canon Inc.) was charged with 5 ml of a water-based yellow DNA ink, sheets of paper were printed using a printer (Canon PIXUS-850i). Fifteen sheets of paper were printed out, and the DNA was recovered from the eighth, ninth and tenth printed sheets by direct DNA transfer. The direct DNA transfer was carried out by drying portions printed with the DNA ink at room temperature for one day, putting 10 μl of $H_2O$ on the portions, pipetting 5 times after 5 seconds, and recovering the DNA.

As for a water-based black DNA ink, a 0.2 μl amount was spotted on sheets of paper and they were dried at 60° C. for 24 hours. The sheets were subjected to the direct DNA transfer under the same conditions as those described above to recover the DNA.

Next, the recovered solutions were subjected to centrifugal filtration using TAKARA SUPREC 02 as a centrifuge column for filtration. The column was firstly washed and then charged with samples (recovered solution 10 μl, TE 90 μl), and the centrifugal filtration was carried out at 1,000 g for 15 minutes to recover (Sample I). Furthermore, the residue left on the column membrane was mixed with 20 μl of TE, and the centrifugal filtration was carried out at 1,000 g for 2 minutes to recover Sample II.

The PCR of a DNA recovered from a DNA ink was carried out 30 cycles at a denaturing temperature of 94° C., an annealing temperature of 55° C., and an extending reaction temperature of 72° C., and each at 30-second intervals (BioTag 2.5 units, template 1 μl, total vol. 50 μl). The buffer composition followed the maker's protocol.

Figure 1:
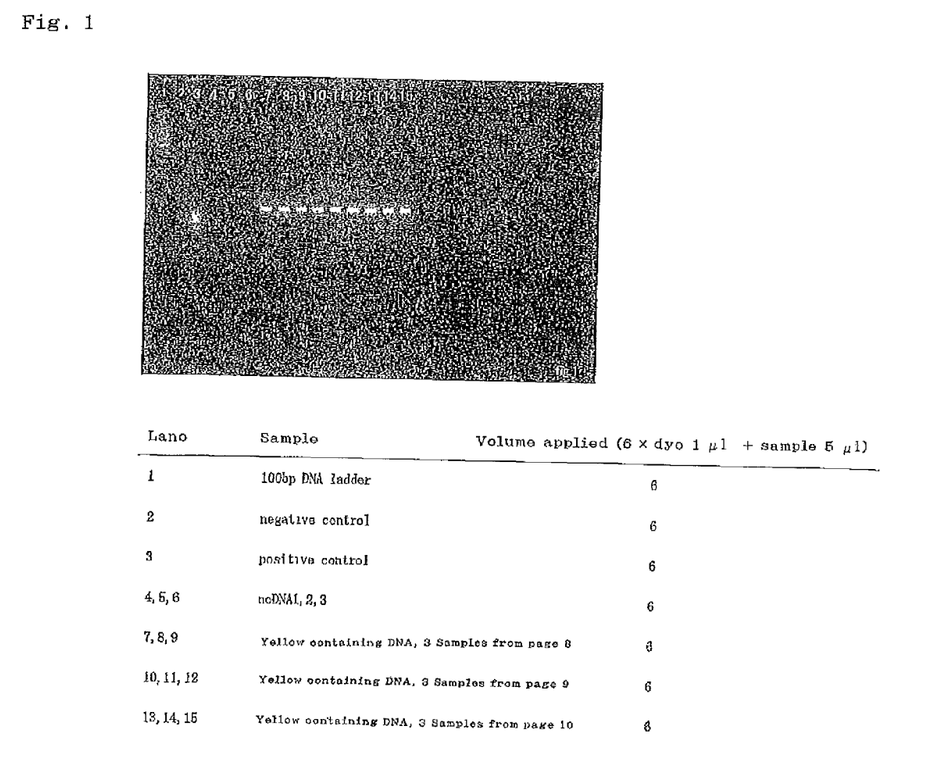
FIG. 1 shows results obtained by recovering a DNA from a water-based ink composition containing the DNA and a yellow dye, and carrying out a PCR analysis.
Figure 2:
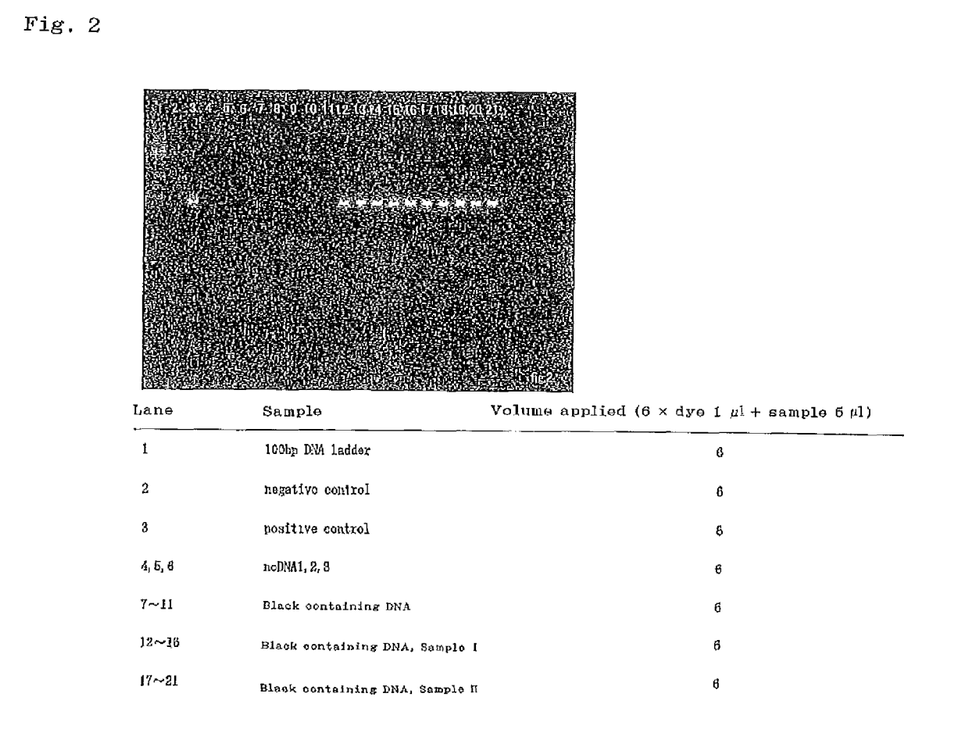
FIG. 2 shows results obtained by recovering a DNA from a water-based ink composition containing the DNA and a black dye, and carrying out a PCR analysis.

Electrophoresis was carried out using 3% agarose gel (0.5× TBE 200 ml, EtBr 10 μg/ml). The results are shown in FIG. 1 and FIG. 2.

In the case of a water-based black DNA ink, amplification was not observed at all in lanes 7 to 11 in which filtration was not carried out as in Comparative Examples 4 and 5, but amplification was confirmed in all lanes 12 to 21 in which filtration was carried out.

When an ink-jet ink is water-based and a dye is black, the leaked samples inhibited the PCR. However, it is thought that the inhibition of the PCR by a dye or a vehicle as ink components could be prevented by filtration of the samples. Also, it was found that DNAs are not cleaved even when an ink-jet ink is injected from a small nozzle in a high pressure when printing. In particular, it was found from the detection results by electrophoresis after the PCR reaction that DNAs having about 85 bases are not cleaved. Although techniques for producing DNA chips by an ink-jet system are recently developed, the above findings suggest a possibility that the DNA chips can be produced without decomposing a DNA by the ink-jet system, when the DNA has 100 or less bases. Also, it was found that a DNA can be detected by recovering an ink by direct DNA transfer and in principle carrying out a PCR reaction, even when a DNA ink is prepared using not only a waterproof ink but also any types of inks, by a removal of ink components by a filter (particularly a dye or a vehicle).

The invention claimed is:

1. A waterproof DNA ink composition comprising water, titanium oxide, isopropanol, resin and a DNA wherein the content of the DNA is 50 pg to 100 ng per 1 ul of the ink composition.

2. The DNA ink composition according to claim 1, wherein the resin is at least one selected from the group consisting of a urethane resin, an acrylic resin, and an epoxy resin.

3. A method of extracting a DNA from a print on a medium, which comprises the step of bringing a print, which is prepared using the DNA ink composition according to claim 1, into contact with water or an aqueous solution.

4. The method according to claim 3, wherein the medium is one selected from the group consisting of paper, a plastic resin, a fabric, a metal, and a food.

5. A method of judging the authenticity of a print on a medium, which comprises the steps of:
   bringing a print, which is prepared using the ink composition according to claim 1, into contact with water or an aqueous solution;
   preparing an aqueous DNA-containing solution obtained by bringing the print into contact with water or an aqueous solution; and
   analyzing the DNA in the aqueous DNA-containing solution prepared.

6. The method according to claim 5, wherein the medium is one selected from the group consisting of paper, a plastic resin, a fabric, a metal, and a food.

* * * * *

SEQUENCE LISTING

```
<160> NUMBER OF SEQ ID NOS: 1

<210> SEQ ID NO 1
<211> LENGTH: 85
<212> TYPE: DNA
<213> ORGANISM: Artificial Sequence
<220> FEATURE:
<223> OTHER INFORMATION: oligonucleotide

<400> SEQUENCE: 1
```

```
attaaccctc actaaaggga tcaataaaac aaaacaaaac gcgcggctca cgggcgccta        60
ggagtgccct atagtgagtc gtatt                                             85
```